(12) United States Patent
Forsell

(10) Patent No.: US 8,147,543 B2
(45) Date of Patent: Apr. 3, 2012

(54) ARTIFICIAL VALVE FOR IMPLANTATION AND RELATED METHODS

(75) Inventor: Peter Forsell, Zug (CH)

(73) Assignee: Thoraxica AG, Baar (CH)

( * ) Notice: Subject to any disclaimer, the term of this patent is extended or adjusted under 35 U.S.C. 154(b) by 0 days.

(21) Appl. No.: 11/591,290

(22) Filed: Nov. 1, 2006

(65) Prior Publication Data

US 2007/0225802 A1 Sep. 27, 2007

Related U.S. Application Data

(60) Provisional application No. 60/732,477, filed on Nov. 2, 2005.

(51) Int. Cl.
*A61F 2/24* (2006.01)
(52) U.S. Cl. ........................ 623/2.28; 623/2.3
(58) Field of Classification Search ........ 623/3.15–3.24, 623/2.2–2.34, 2.1; 137/625.3, 625.31; 251/208; *A61F 2/24*
See application file for complete search history.

(56) References Cited

U.S. PATENT DOCUMENTS

| | | | | |
|---|---|---|---|---|
| 3,771,173 A | * | 11/1973 | Lamb, Jr. | 623/3.28 |
| 4,304,261 A | * | 12/1981 | Forester | 137/613 |
| 4,599,081 A | * | 7/1986 | Cohen | 623/2.34 |
| 4,623,350 A | * | 11/1986 | Lapeyre et al. | 623/3.17 |
| 4,674,537 A | * | 6/1987 | Bergmann | 137/625.31 |
| 5,181,580 A | * | 1/1993 | Burg | 180/116 |
| 5,326,374 A | | 7/1994 | Ilbawi et al. | |
| 5,342,025 A | * | 8/1994 | Hwang | 251/65 |
| 6,979,351 B2 | * | 12/2005 | Forsell et al. | 623/3.1 |
| 7,238,165 B2 | * | 7/2007 | Vincent et al. | 604/6.11 |

(Continued)

FOREIGN PATENT DOCUMENTS

EP 0102548 3/1984

(Continued)

OTHER PUBLICATIONS

International Search Report for PCT/EP2006/010379 dated May 3, 2007.

(Continued)

*Primary Examiner* — Thomas J Sweet
*Assistant Examiner* — Jason-Dennis Stewart
(74) *Attorney, Agent, or Firm* — Nixon & Vanderhye P.C.

(57) ABSTRACT

An artificial valve (100) and related methods are provided for implantation in a patient's blood vessel (200), in particular an artificial heart valve, including a first (10) and a second (20) valve member each having a first smooth surface (11, 21) facing each other so as to form a sealing contact between the first and second valve members and further having at least one blood flow passage (13, 23*a*) extending from the first surface to a second surface (12, 22) located on an opposite side of the respective valve member, wherein at least one (10) of the valve members is arranged so as to be displaceable relative to the other (20) valve member in a slidable manner such that the passage (23*a*) of the second valve (20) member can be brought into at least partial alignment with the passage (13) of the first valve member (10) while maintaining the sealing contact between the first and second valve members, and a displacing mechanism (M; 50-56) for the relative displacement of the valve members (10, 20). The valve members can be made from ceramics. A valve system comprises the artificial valve (100) and additional components such as a motor (M), an energy source (E), a control unit (C), a pressure sensor (P), a feed back system and/or an alarm system.

94 Claims, 9 Drawing Sheets

U.S. PATENT DOCUMENTS

| | | |
|---|---|---|
| 2002/0072698 A1* | 6/2002 | Chiang et al. ............ 604/6.11 |
| 2003/0069547 A1 | 4/2003 | Gonon |
| 2004/0024285 A1* | 2/2004 | Muckter .................... 600/16 |
| 2004/0068299 A1 | 4/2004 | Laske et al. |
| 2004/0098113 A1* | 5/2004 | Forsell et al. ............ 623/1.25 |
| 2005/0060030 A1* | 3/2005 | Lashinski et al. ......... 623/2.37 |
| 2005/0222678 A1* | 10/2005 | Lashinski et al. ......... 623/2.11 |
| 2006/0025855 A1* | 2/2006 | Lashinski et al. .......... 623/2.1 |
| 2006/0074484 A1* | 4/2006 | Huber ..................... 623/2.11 |
| 2006/0178552 A1 | 8/2006 | Gross |
| 2007/0204924 A1* | 9/2007 | Delgiacco et al. ...... 137/625.31 |
| 2007/0276480 A1* | 11/2007 | Tansley et al. ............ 623/3.13 |

FOREIGN PATENT DOCUMENTS

| | | |
|---|---|---|
| EP | 0412191 | 2/1991 |
| EP | 1 514 526 | 3/2005 |
| EP | 1563814 | 8/2005 |
| EP | 1563886 | 8/2005 |
| GB | 1 194 358 A | 6/1970 |
| GB | 1194358 | 6/1970 |
| WO | WO 84/01282 | 4/1984 |
| WO | WO 02/40083 | 5/2002 |
| WO | WO 02/087657 | 11/2002 |
| WO | 2007/051568 A2 | 5/2007 |

OTHER PUBLICATIONS

PCT International Search Report for PCT application No. EP2006/010349 dated Feb. 12, 2007.

International Search Report for PCT/EP2010/060080; Mail Date Sep. 27, 2010.

* cited by examiner

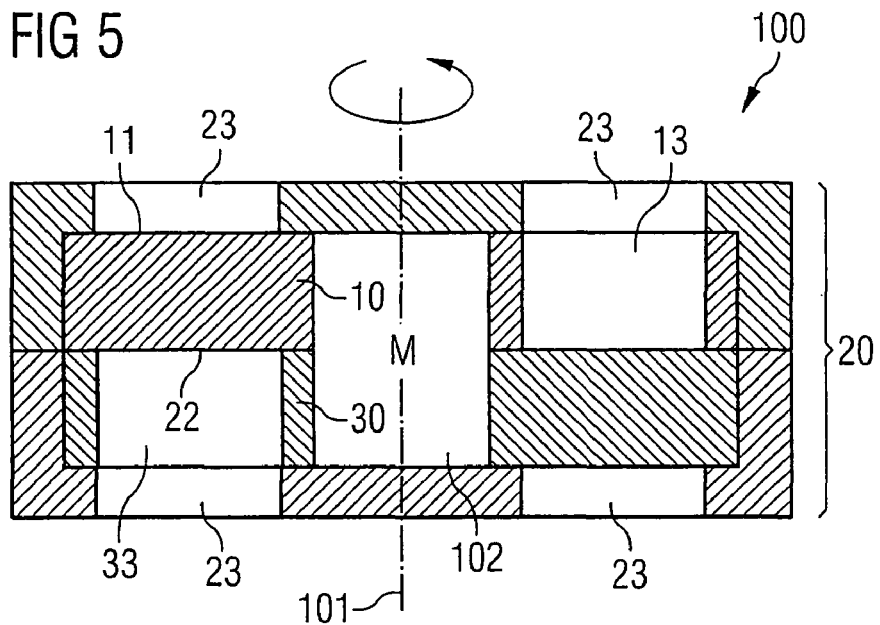
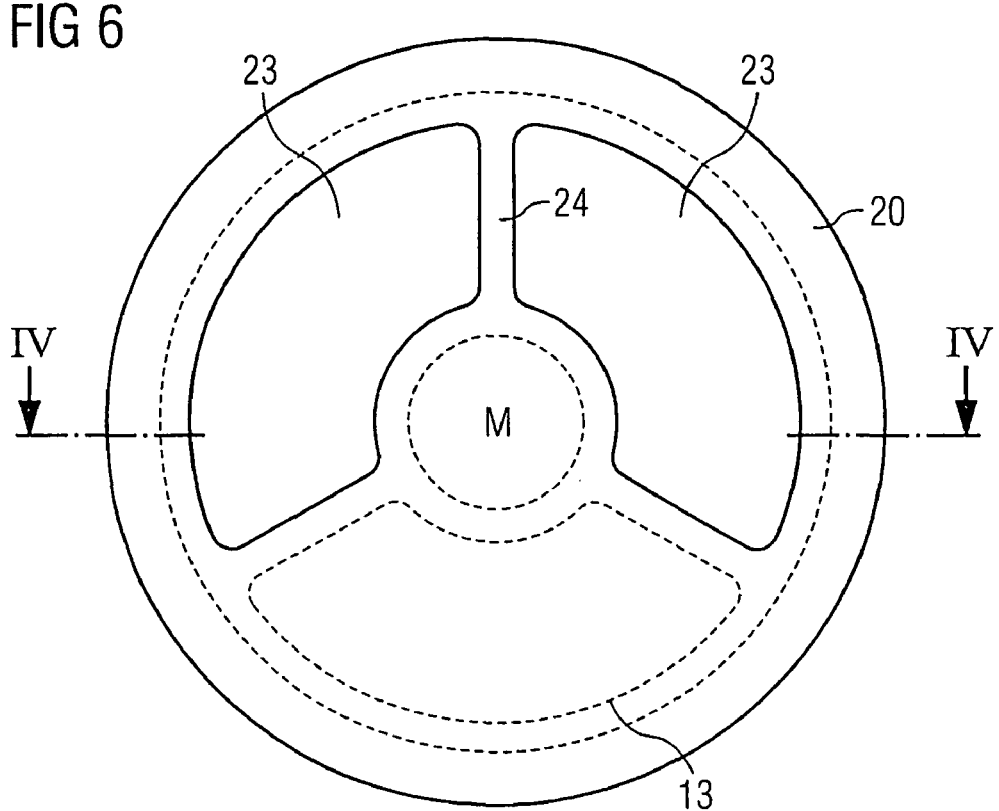

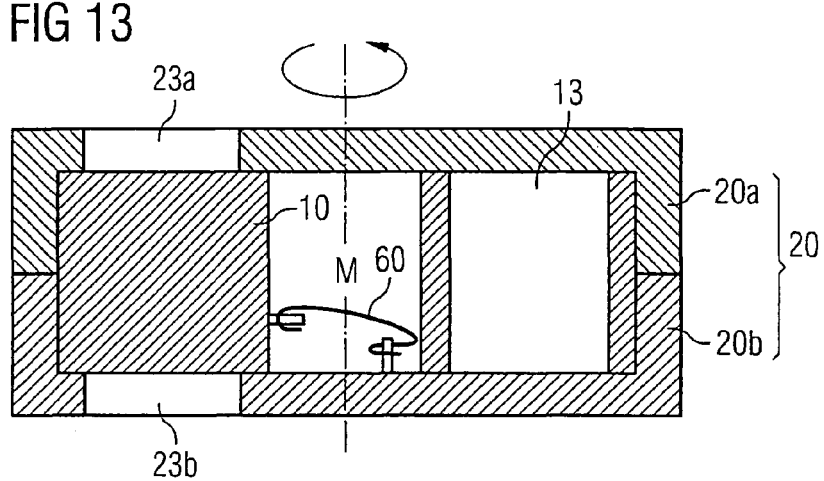
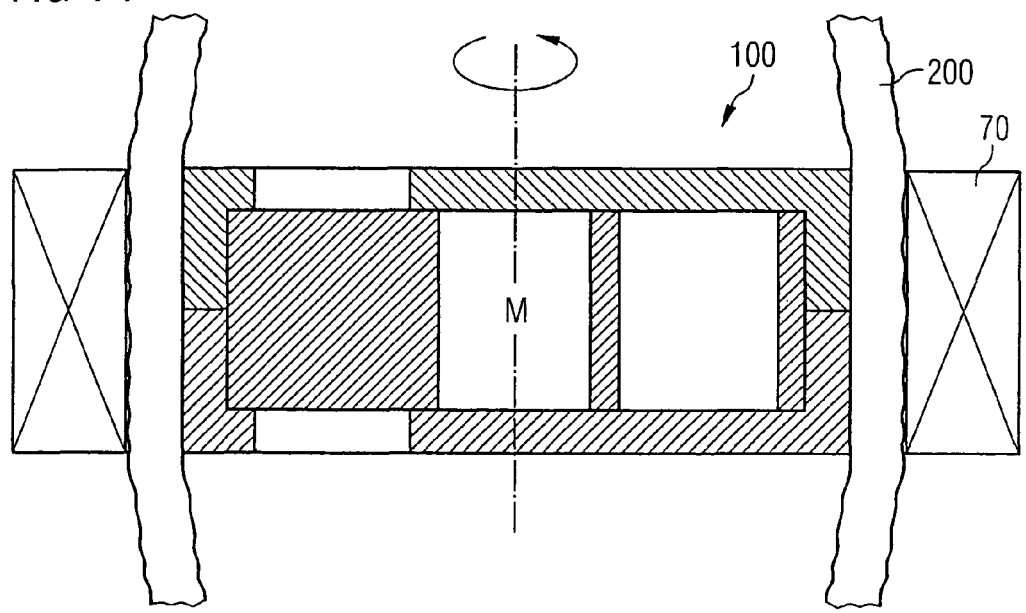

ARTIFICIAL VALVE FOR IMPLANTATION AND RELATED METHODS

RELATED APPLICATIONS

The presently disclosed subject matter claims the benefit of U.S. Provisional Patent Application Ser. No. 60/732,477 filed Nov. 2, 2005; the disclosure of which is incorporated herein by reference in its entirety.

BACKGROUND

The present subject matter relates to an artificial valve and related methods for implantation in a patient's blood vessel, in particular an artificial heart valve, and further relates to a valve system including such an artificial valve.

Artificial heart valves are generally designed to replace the natural heart valve and to perform its function over many years, preferably until the person (or animal) dies. Thus, besides the general requirement that artificial valves must be made from a material that is compatible with the patient's blood and tissue, the valve must furthermore be extremely reliable.

Typical artificial heart valves are strictly mechanical, such as mechanical mono- or bi-leaflet valves and ball valves. A leaflet valve may for instance comprise a tilting disc hinged to an annular ring that is sutured into the blood vessel. The blood pressure changes of typically between 80 mmHg and 120 mmHg cause the disc to swing between an open and a closed position. In ball valves, a ball is held in a cage and allowed to move therein upon blood pressure changes between a closed position in which it seals an annular ring sutured into the blood vessel and an open position in which the ball is at a distance from the ring, thereby permitting blood to flow around the ball.

While there are many different types of artificial valves for implantation in a patient's blood vessel, they all suffer from the draw back of material fatigue resulting in breakage of parts thereof. Disfunctioning of the valve is only one severe consequence thereof. The consequences may be fatal when broken parts are carried away with the blood stream and block the blood stream at remote locations. Another problem arising with artificial valves implanted in blood vessels is the danger of generating thromboses as well as fibrosis forming and growing on the valve elements. Particularly the latter may prevent complete closing of the valve, thereby causing valve insufficiency.

SUMMARY

It is therefore an object of the present subject matter to provide an artificial valve and related methods for implantation in a patient's blood vessel, in particular an artificial heart valve, which is mechanically reliable over a long period of time without its closing efficiency being substantially affected by fibrosis.

It is a further object of the present subject matter to provide a valve system comprising such an artificial valve and further components.

Accordingly, the artificial valve of the present subject matter comprises a first and a second valve member, each having a first smooth surface. The first smooth surfaces of the first and second valve members face each other so as to form a sealing contact between the first and second valve members. The first and second valve members further each have at least one blood flow passage extending from the first smooth surface to a second surface located on an opposite side of the respective valve member, wherein at least one of the valve members is arranged so as to be displaceable relative to the other valve member in a slidable manner such that the passage of the second valve member can be brought into at least partial alignment with the passage of the first valve member while maintaining the sealing contact between the first and second valve members. The artificial valve according to the present subject matter further comprises a displacing mechanism for the relative displacement of the valve members so as to bring their blood flow passages into and out of said at least partial alignment.

This way, blood flow through the valve can be controlled by sliding displacement of the valve members relative to one another, thereby aligning and disaligning the blood flow passages, i.e. opening and closing the valve. The smooth surfaces forming the sealing contact and the fact that opening and closing of the valve is performed by sliding displacement of the smooth surfaces relative to each other prevent any fibrosis formation on the sealing surfaces. Thus, the sealing efficiency will not deteriorate over time. Furthermore, due to the valve members being displaced relative to one another in a sliding fashion, the forces acting on the valve members are relatively small, thereby overall reducing problems of fatigue of the valve member material.

The theoretical maximum flow capacity of an artificial valve according to the present subject matter with only two valve members amounts to only about 50% of a fully opened natural valve for the simple reason that each of the two valve members must have a closed area sufficiently large to cover and close the flow passage of the respective other valve member when the valve is in its closed position. Therefore, according to one aspect, the artificial valve can comprise three valve members or, more preferably, even more than three valve members, arranged in series. The third valve member also has a first smooth surface which, however, is arranged to form a sealing contact with the second, preferably smooth surface of the first valve member and further has at least one blood flow passage extending from its first smooth surface to a second surface located on an opposite side of the third valve member. The third valve member is arranged so as to be displaceable relative to the first valve member in a slidable manner such that the passage of the third valve member can be brought into at least partial alignment with the passages of the first and second valve members while maintaining the sealing contact between the first and third valve members. Similarly, one or more further valve members may be added, each having a first smooth surface for sealingly contacting a preferably smooth second surface of one of the other valve members and also having a blood flow passage for at least partial alignment with the passages of the other valve members.

Providing more than two valve members in the manner described above allows for enlarging the flow capacity of the artificial valve. For instance, in the case of three valve members, only a third of the cross sectional area of each valve member must be closed, i.e. fluid tight, so that by appropriate arrangement of the valve members relative to each other the entire cross sectional area of the artificial valve may be closed.

The valve members may be arranged so as to be slidable back and forth relative to one another in opposite directions or so as to be slidable in a single direction. In the former case, the valve members may be arranged so as to be linearly slidable, such as in a direction perpendicular to the extending direction of the blood vessel, so as to allow for the at least partial alignment of their blood flow passages. More preferably, however, the displaceable arrangement of the valve members relative to one another is such that the valve members are rotatable. This allows for the at least partial alignment and disalignment of their blood flow passages either by moving the valve members back and forth in opposite directions or by continuously moving them in a single direction. In the latter case, it is preferred that the blood flow passages in each of the valve members are identically arranged about a common axis so as to maximize their rate of overlap when the valve is in its open position.

As mentioned above, the flow capacity of the valve can be increased by increasing the number of displaceably arranged valve members. In the case of rotatably arranged valve members, the flow passage of each of the valve members preferably has an angular extension about the common axis of 360×n/(n+1), where n is the number of the displaceably arranged valve members. More preferably, the angular extension is somewhat less than this to ensure complete cross sectional overlap of the valve members when the valve is in its closed position.

However, where the artificial valve includes more than two valve members, e.g. three valve members each having a blood flow passage with an angular extension of 240°, the blood flow passages of each pair of adjacent valve members overlap by 120°. As a result, backflow in a plane substantially perpendicular to the axis of rotation will occur in the valve's closed position even though, when viewed in a direction along the axis of rotation, the valve members completely cover the entire cross section of the valve. To prevent such backflow, a preferred embodiment of the subject matter provides for dividing the blood flow passages of the valve members into sections by means of more or less radially extending bridges. These bridges are located at positions so as to prevent in the valve's closed position any backflow from the passage of one valve member through the passage of the next adjacent valve member to the passage of the next over adjacent valve member. In the case of three valve members, it would be sufficient to have such a bridge at least in the passage of the centrally arranged valve member so as to separate the passage of the upper valve member from the passage of the lower valve member.

Thus, where there is only one displaceable valve member (one or more further valve members being stationary), no bridge would be required, whereas in the case of two displaceably arranged valve members, as in the case of the three valve members discussed above with one valve member being stationary, at least one bridge would be required. Generally, the number of bridges is n−1, where n is the number of the displaceably arranged valve members.

Of course, the number of bridges can be larger than n−1 and this is even preferred in order to divide the passages into a plurality of angularly extending sections which can be equally distributed about the axis of rotation. As a result, the blood flow through the artificial valve is distributed more evenly over the valve's cross section.

In that case, the bridges of each valve member preferably each have a radially extending center line, wherein the center lines are arranged about the common axis at an equal angular distance and the bridges each have an angular extension equal to or preferably somewhat larger than the angular extension of each of the sections. The advantage of such an arrangement can be easily appreciated for a valve with only two valve members, the passages of which each have an overall angular extension of 180° (or somewhat less), but are subdivided into e.g. four sections of 45° equally spaced apart about the common axis. Instead of turning the valve member by 180° to bring the blood flow passages of the two valve members into alignment, it is sufficient to turn the valve members by only 45°.

At least two or all of the surfaces together forming a sealing contact are preferably parallel, i.e. the sealing surfaces lie in parallel planes. While the sealing surfaces can be stepped, it is preferable for reason of easy manufacture that the sealing contact is overall flat. Alternatively, at least two or all of the surfaces together forming a sealing contact may have cooperating concave and convex shapes. This is particularly suitable for rotatable valve members and has the advantage that the valve members are self aligning in response to the blood pressure acting on their exterior surfaces.

Good performance of the valve's mechanism is obtained when the valve members are made of a material inert enough to maintain over time a low friction between the surfaces forming the sealing contact. This eliminates the risk of the smooth surfaces sticking to each other. Most preferably, the valve members are made of a ceramic material. Ceramic works better than most metals, which, when mounted together with fine tolerances between surfaces, will more easily stick together over time. More particularly, with every relative sliding movement the sealing properties of ceramic sealing surfaces will even improve over time. Preferably, the entire valve is made from ceramics with one of the valve members forming a housing for the valve.

For use in an individual's blood vessel, the artificial valve is designed such that the sealing contact formed by two of the surfaces withstands without leaking an internal positive diastolic pressure of at least 80 mmHg (1.05 N/cm2). Of course, the surfaces should not be pressed together with extensive forces but their sealing capabilities should be sufficient even at minimum axial pressure. More particularly, the valve members should be mounted so as to barely contact each other and preferably so as to even protected against any axial pressure caused by the blood pressure. Under such circumstances, the sealing capability of the contacting sealing surfaces is substantially a function of the maximum roughness and the maximum unevenness of the sealing surfaces as well as the minimum contact length between one of the passages and an outer border of one of the corresponding two sealing surfaces, i.e. the minimum distance that blood particles would have to travel from inside the passages to outside the valve members. Depending on the needs of pressure limit for sealing the contact surfaces, one or more of these parameters may be changed. Also the leakage may be very low and unimportant and, therefore, the blood pressure of 80 mmHg does not need to be a limit for sealing the contact surfaces. When improving the sealing capabilities, producing the contact surfaces with very little roughness or very good evenness may be more expensive than increasing the contact length between the sealing surfaces.

Therefore, the two surfaces forming together said sealing contact should each have a maximum roughness good enough to substantially avoid leakage through said sealing contact, taking the other parameters into account. Furthermore, the two surfaces forming together said sealing contact should each have a maximum unevenness over the entire contact area good enough to substantially avoid leakage through said sealing contact, taking the other parameters into account. Finally, with respect of the two surfaces forming together said sealing contact, the minimum contact length between one of the corresponding passages and an outer border of one of the two surfaces should be large enough to substantially avoid leakage through said sealing contact, taking the other parameters into account.

The maximum roughness and maximum unevenness of ceramics depend on the production method, but for plates they are normally very good and still within reasonable production costs. Of course, deviations to the disadvantage of one of the three aforementioned factors can be compensated by corresponding deviations to the advantage of one or both of the respective other two aforementioned factors.

A pretensioning element may be provided by which the valve members are urged together. However, the pretensioning force should be minimal for the reasons mentioned above. Strong pretensioning forces could increase the friction between the valve members and, thus, negatively influence the valve's efficiency.

Preferably, an exposed surface of the heart valve on the upstream and/or downstream side of the heart valve is designed to provide for a laminar blood flow along substantially the entire surface area under in vivo conditions so as to prevent the build up of fibrosis, which tends to build up in dead zones of the blood flow. Also, blood tends to coagulate in dead zones, causing an increased risk of thrombosis.

According to the present subject matter, a displacing mechanism is provided for the relative displacement of the valve members. Such displacing mechanism is preferably mechanically driven by forces exerted by the blood pressure, so as to be independent of any external energy. Nevertheless, a motor may be provided as a safety backup, coming into action e.g. in case of malfunctioning of the valve, such as blocking of the valve members.

According to one aspect, the blood-pressure driven displacing mechanism may comprise a pressure transforming member arranged for transforming, when the valve is implanted in a patient's blood vessel, a blood pressure change into relative movement of the displaceably arranged valve members. For instance, the pressure transforming member may comprise a pressure plate or diaphragm arranged to be movable by changes of the blood pressure acting on the valve, and mechanically coupled to at least one of the displaceably arranged valve members. Preferably, such pressure plate or diaphragm is positioned on an upstream side of the valve and coupled to at least one of the valve members such that increased blood pressure acting on the valve on the upstream side of the valve causes the pressure plate or diaphragm to move in a downstream direction and, thereby, further causes at least partial alignment of the valve members. Thus, when the blood pressure on the upstream side of the valve, such as in a heart chamber, increases sufficiently to overcome a counterpressure, such as the blood pressure on the downstream side or forces exerted by a return spring, the valve will automatically open by relative displacement of the valve members.

The pressure plate or diaphragm need not necessarily be positioned on an upstream side of the valve but may also be positioned on a downstream side thereof, so that, when the blood pressure on the downstream side decreases below a predetermined value, the valve opens automatically. Most preferably, the valve comprises a pressure plate or diaphragm on both the upstream side and the downstream side of the valve. The valves opens and closes when the pressure difference between the pressure acting on the upstream side and the pressure acting on the downstream side becomes positive and negative, respectively. This can be achieved, e.g. by rigidly connecting the pressure plate or diaphragm on the upstream side of the valve to the pressure plate or diaphragm on the downstream side of the valve.

Instead of or in addition to being mechanically blood-pressure driven, the displacing mechanism may comprise a motor for bringing the blood flow passages of the valve members into and out of alignment. Such a motor is preferably incorporated in the valve so as to be implantable into the blood vessel along with the valve as a single device. More preferably, the motor may be contained within a valve housing which is sealed against blood ingression. The valve housing may be formed and at the same time sealed against blood ingression by the valve members. More particularly, the motor may be incorporated within a cavity formed in a central area of the valve members.

While the motor may be driven e.g. by electricity provided to the motor either directly or indirectly, in a preferred embodiment the motor is arranged for being driven by an electromagnetic field. This allows for arrangement of a stator outside the blood vessel and the rotor inside the valve, the rotor being connected to one ore more of the displaceably arranged valve members.

As a safety measure, means may be provided to urge the blood flow passages into at least partial alignment when the motor is not energized, so that the valve cannot block in the case of malfunctioning of the motor. Such means may comprise a return spring arranged for relative movement of the valve members so as to bring the flow passages into at least partial alignment.

There are a number of preferred ways for supplying the motor with energy. Such an energy source may be a primary energy source, but it may also or alternatively comprise energy storage means, such as a battery or an accumulator, such as a rechargeable battery and/or capacitor. The accumulator may be rechargeable from outside the blood vessel by wire or, more preferably, wirelessly.

Alternatively, the rechargeable battery or capacitor or any other energy storage means may be charged by energy taken from the blood flow. More particularly, the energy source for the motor may comprise a blood flow energy transforming device for transforming blood flow energy into electrical energy when the energy source is implanted in a patient's blood vessel, this electrical energy being used for charging the energy storage means or, alternatively, for direct use by the motor, or both. For instance, the blood flow energy transforming means may comprise an impeller arranged in the blood flow so as to be turned by the blood flow.

The energy source for providing the motor with energy need not necessarily be part of the valve but may alternatively be placed outside the blood vessel either within the patient's body or even outside the patient's body, such as on the patient's skin. Again, the energy source may comprise energy storage means along with or separate from energy supply means, such as a capacitor, a rechargeable battery and/or any other type of accumulator, for temporarily storing energy supplied by a primary energy source. The energy source may also consist of a battery to be replaced from time to time. Where the energy source comprises means for supplying energy from outside the patient's body, the accumulating energy storing means may be implanted inside the patient's body, either inside the blood vessel along with the valve or outside the blood vessel, preferably under the skin to be easily accessible or in the abdomen if there are space constraints. Placing the accumulating energy storing means inside the patient's body is more comfortable for the patient for it is not visible or awkward.

The energy transfer from outside the patient's body to the motor and/or to the energy storage means inside the patient's body can be performed either wirelessly or by wire, i.e. via galvanic coupling elements, or both. For instance, an energy transmission device for wireless energy transfer from outside the patient's body to an energy storage means implanted inside the patient's body may be combined with galvanic coupling between the energy storage means and the motor, regardless of whether the energy storage means is part of the valve or is placed within the patient's body outside the blood vessel. Alternatively, the energy may be transferred wirelessly from the energy storage means to the motor.

The motor may be adapted to directly transform the wirelessly transferred energy. Any additional accumulating energy storage means may serve as a backup, storing surplus energy not immediately consumed by the motor.

Instead of directly using the wirelessly transferred energy by the motor, such as in the case of an electromagnetically driven motor, a transforming device for transforming the wirelessly transferred energy into electric energy may be provided. Such a transforming device is preferably adapted to be placed directly under the patient's skin so as to minimize the distance and the amount of tissue between the transforming device and the energy supply means outside the patient's body.

The energy transmission device for wireless energy transfer from the energy source and/or energy storage means to the motor may be adapted to generate an electromagnetic field, as discussed above in respect of the electromagnetically driven motor. Alternatively or in addition, the energy transmission device for wireless energy transfer may be adapted to generate a magnetic field. Also, the energy transmission device for wireless energy transfer may be adapted to generate an electrical field. The wireless energy may be transmitted by the energy transmission device by at least one wireless signal. Such signal may comprise an electromagnetic wave signal, including at least one of an infrared light signal, a visible light signal, an ultraviolet light signal, a laser signal, a microwave signal, a radio wave signal, an X-ray radiation signal and a radiation signal. Also, the wireless energy signal may comprise a sound or ultrasound wave signal. Furthermore, the wireless energy signal may comprise a digital or analog signal or a combination thereof.

Instead of wireless energy transfer from outside the patient's body into the patient's body, the valve system may comprise galvanic coupling elements adapted to connect the energy storage means, when implanted inside the patient's body, or the motor to an extracorporal primary energy source for transmitting energy to the energy storing means or motor, in contacting fashion. The extra corporal primary energy source may form a part of the overall valve system.

The valve system according to the present subject matter may further comprise a control unit for controlling the motor of the valve so as to bring the blood flow passages into and out of alignment in conformity with a control signal.

The control unit may be adapted for implantation inside the patient's body either outside the blood vessel or inside the blood vessel. In the latter case, the control unit preferably forms an integral part of the artificial valve. Alternatively, the control unit may be adapted for controlling the motor from outside the patient's body and may, thus, be mounted on the patient's skin. The latter alternative allows for direct manipulation of the control unit by a doctor or by the patient by appropriate manipulation of the control unit.

A control signal transmission device may be provided for wireless transmission of the control signal to the motor. Similarly, a data transmission interface for wirelessly transmitting data from outside the patient's body to the control unit inside the patient's body may be provided. Again, the wireless control signal and/or data transmission may comprise one of the aforementioned wave signals, being digital or analog or a combination thereof. More preferably, the control signal is transmitted in the same manner as the energy is transmitted to the motor. For instance, the control signal may be transmitted by modulation of an energy signal, the energy signal thereby serving as a carrier wave signal for the digital or analog control signal. More particularly, the control signal may be a frequency, phase and/or amplitude modulated signal.

While it is generally conceivable that the valve opens and closes according to a predetermined clock cycle, it is preferable that the control signal is influenced by external signals, such as signals depending upon the patient's momentary constitution. More particularly, the control signal may relate to a blood pressure signal. For instance, when the blood pressure on the upstream side of the valve has reached a predetermined level, a control signal causing the valve to open may be sent to the motor.

A preferred embodiment of the valve system according to the present subject matter therefore comprises a blood pressure sensor which provides the blood pressure signal, when the system is installed in a patient. The blood pressure sensor is preferably arranged on an upstream side of the valve and may be located e.g. in a heart chamber. Most conveniently, the blood pressure sensor may be fixed to an exterior surface of the valve.

The control signal may alternatively or additionally relate to a pacemaker signal. Therefore, the valve system according to the present subject matter preferably further comprises a pacemaker which, when the system is installed in a patient, provides the pacemaker signal to the control unit or may even directly provide the pacemaker signal to the motor. In the latter case the pacemaker may replace or include the control unit of the valve system.

The control unit may be freely programmable so as to be flexibly adaptable to provide control signals for the motor according to changing demands. For the sake of convenience, it is preferred that the control unit is programmable from outside the patient's body. In case the control unit is adapted for being implanted inside the patient's body, the control unit is preferably programmable by wireless remote control. A programming unit adapted for programming the control unit may complete the valve system. Such programming unit may be mountable on the patient's skin.

Furthermore, the control unit may be adapted to provide feedback information. Where the control unit is arranged for implantation in the patient's body, feedback information can be transferred to the outside in the same manner as programming from the outside is performed, i.e. preferably wirelessly. The feedback information may not only relate to physiological data of the person, such as blood pressure data, but may also relate to technical data of the valve system.

Furthermore, the valve system of the present subject matter may comprise an alarm system. An alarm may automatically prompt appropriate action to be taken by the system, in particular by the control unit, or may simply alert the patient to any malfunctioning within the system. For instance, the alarm system may comprise a blood pressure sensor which may be the same as the one mentioned above. If, for instance, the valve comprises a blood-pressure driven displacing mechanism, an alarm sent by the blood pressure sensor may indicate improper functioning of the valve and prompt the control unit to activate a motor provided as a safety backup. The blood pressure sensor is preferably arranged on an upstream side of the valve.

It is therefore an object of the present subject matter to provide a novel artificial valve for implantation and related methods. An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 5 shows a cross sectional view of another embodiment of the artificial valve according to the present subject matter with two rotatable valve members.

FIGS. 6 and 7 show top views of different designs of the artificial valve shown in FIG. 5 with differently arranged flow passages.

FIG. 13 shows an artificial valve including a motor and a return spring intended to urge the valve into an open state when the motor is not energized.

FIG. 14 shows an artificial valve where the motor is driven electromagnetically from outside the blood vessel.

DETAILED DESCRIPTION OF DRAWINGS

Figure 1:
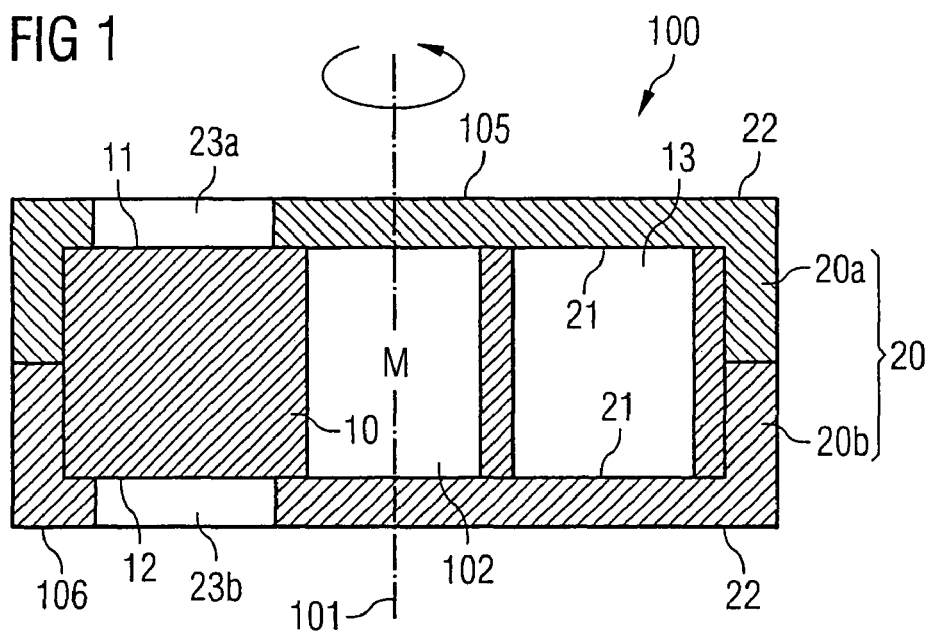
FIG. 1 shows a cross section of an embodiment of the artificial valve according to the present subject matter with one rotatable valve member.

FIG. 1 shows an artificial valve 100 comprising a first valve member 10 and a second valve member 20, composed of two halves 20a, 20b. In this embodiment, the second valve member 20 forms a housing for the first valve member 10. The first valve member 10 is disc-shaped and arranged within the second valve member 20 for rotation about an axis 101, while the second valve member 20 is stationary. The first valve member 10 has a blood flow passage 13 extending from a first surface 11 to a second surface 12, and the second valve member has a blood flow passage 23a, 23b extending from a first inner surface 21 to a second outer surface 22. Upon rotation of the first valve member 10 about the axis 101, the blood flow passage 13 of the first valve member 10 may be brought into complete alignment with the blood flow passage 23a, 23b of the second valve member 20, thereby establishing flow communication through the valve 100 from an upstream side 105 to a downstream side 106 thereof.

FIG. 1 merely shows the principle of the artificial valve of the present subject matter. The absolute and relative dimensions are therefore not true to scale and the shape of the valve members may be chosen differently. Also, means for monitoring the valve in the blood vessel are not shown.

Preferably, the valve members 10, 20 are made from ceramics since such material provides excellent sealing properties between the sealing surfaces 11, 21 and 12, 21 of the first and second valve members 10, 20, respectively, and since such material is sufficiently inert.

The two halves 20a, 20b of the second valve member 20 may be joined together by welding, fusing or bonding. However, best sealing properties between the sealing surfaces 11, 21 and 12, 21 will be obtained when the two halves 20a, 20b of the second valve member 20 are pressed with minimum pressure against the first valve member 10, as will be more specifically described below in conjunction with FIG. 10.

Centrally arranged within the artificial valve 100 is a displacing mechanism in the form of a motor M for displacement of the first valve member 10 relative to the second valve member 20 for turning the first valve member 10 either back and forth or always in the same direction. The displacing mechanism is contained in a cavity 102 which is formed and sealed against blood ingression by the valve members 10, 20.

Figure 2:
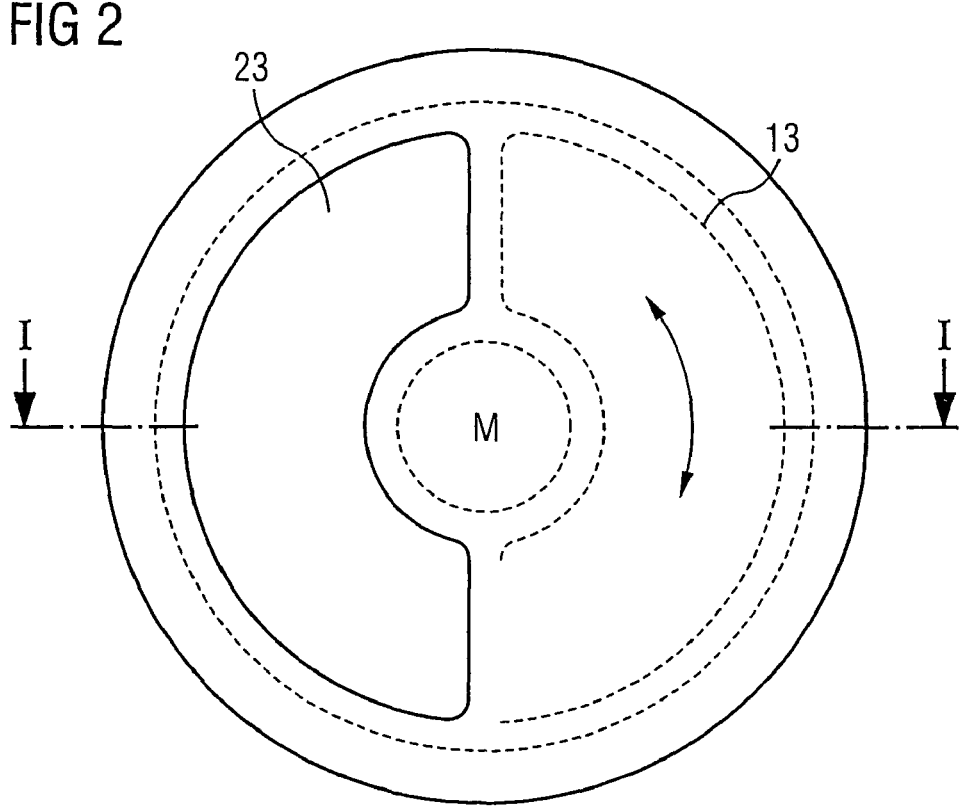
FIGS. 2 to 4 show top views of three different designs of the artificial valve shown in FIG. 1 with differently arranged flow passages.
Figure 3:
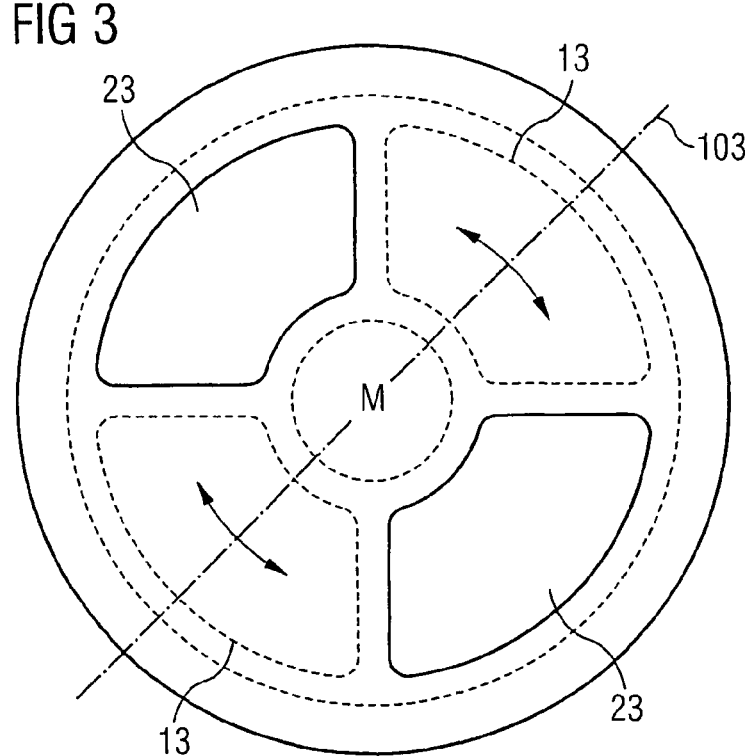
Figure 4:
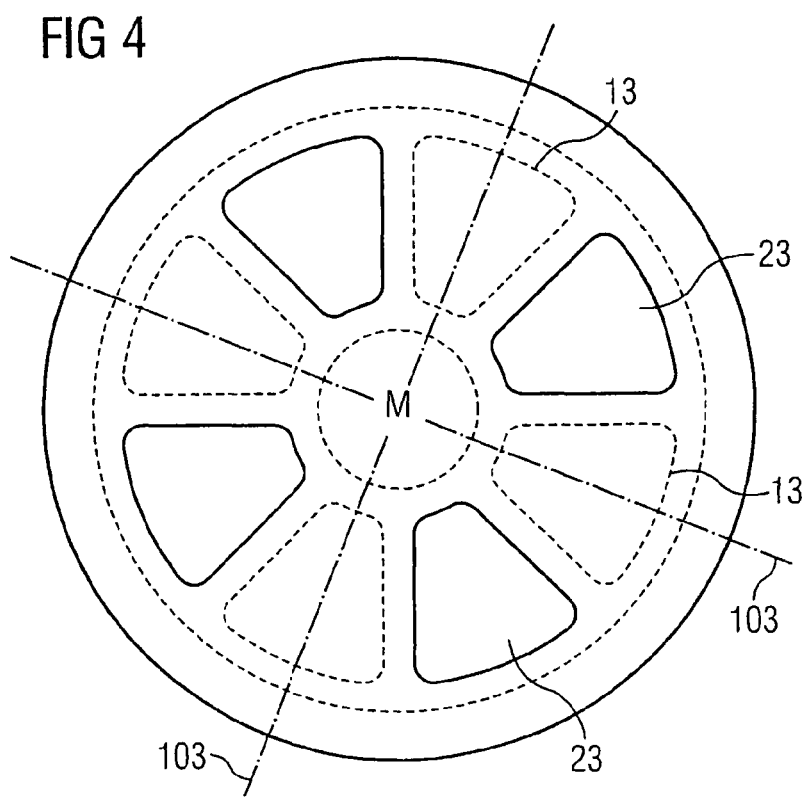

FIGS. 2 to 4 each show a top view of the artificial valve 100 of FIG. 1, but with different blood flow passage designs. In FIG. 2, the blood flow passages 13, 23 each extend over 180° in an angular direction, more particularly somewhat less than 180° so as to prevent any flow communication between the blood flow passages 13, 23 when the valve 100 is in its closed position. Clearly, the rotatably arranged first valve member 10 has to be turned by 180° to open and close the valve. Also, blood flow will be concentrated at one side of the valve 100.

FIG. 3 shows a somewhat improved flow passage design where the blood flow passages 13, 23 have each been separated to form two sections, each with an angular extension of somewhat less than 90°. By this arrangement, rotation of the first valve member 10 by only 90° will already bring the blood flow passages 13, 23 of the first and second valve members into complete alignment. Also, the blood flow through the valve 100 is diverted on two opposing sides of the valve. FIG. 4 shows an even further enhanced embodiment with the flow passages 13, 23 being subdivided into four sections equally spaced apart, each with an angular extension of somewhat less than 45°. Rotation of the first valve member 10 by 45° will be sufficient to bring the flow passages 13, 23 into and out of alignment. The design in FIGS. 3 and 4 is symmetrical and the area between the blood flow passages of a valve member may be described as forming bridges, wherein the bridges of each valve member each have a center line 103 arranged about the common axis 101 with an equal angular distance and having an angular extension equal to or preferably somewhat larger than the angular extension of each of the sections of the blood flow passages.

In the embodiments shown in FIGS. 2 to 4, the passages 13 and 23 have an overall—interrupted or uninterrupted—angular extension about the common axis 101 of exactly or preferably somewhat less than 180°. If, however, more than one displaceably arranged valve member is provided, the angular extension of their respective blood flow passages can be extended, thereby increasing the valve's overall through flow capacity. This can be expressed by an equation in that the angular extension of the blood flow passages may be calculated as $360 \times n(n+1)$, where n is the number of the displaceably arranged valve members.

FIG. 5 shows an embodiment with two displaceably arranged valve members 10, 30 disposed within a housing formed by the second, stationary valve member 20. Again, the valve members 10, 30 are rotatable about a common axis 101 and form a central cavity 102 for accommodating the displacing mechanism or motor M.

FIG. 6 shows a top view of the artificial valve of FIG. 5 with the blood flow passage 23 of the second valve member 20 extending over about 240°. In the specific embodiment of FIG. 5, however, the blood flow passage 23 is subdivided by a radially extending bridge 24 so as to divide the blood flow passage 23 into two sections of equal size. The blood flow passages 13, 33 of the two rotatable valve members 10, 30 are also each subdivided by corresponding bridges so as to form two sections of equal size. This is needed since the blood flow passages 23, 13, 33 partially overlap when the valve is in its closed position and, therefore, backflow in a transverse direction would occur between three adjacent valve members if such bridge was not present. It would actually be sufficient to provide such bridge only in one of the first and third valve members 10, 30 so as to prevent any flow connection from the blood flow passage 23 to the blood flow passage of the next over adjacent valve member.

Clearly, where more than two rotatably arranged valve members are present in the artificial valve, the number of radially extending bridges 24 would have to be increased accordingly. As a general rule, the number of bridges 24 will be n−1, where n is the number of the displaceably arranged valve members.

Figure 7:
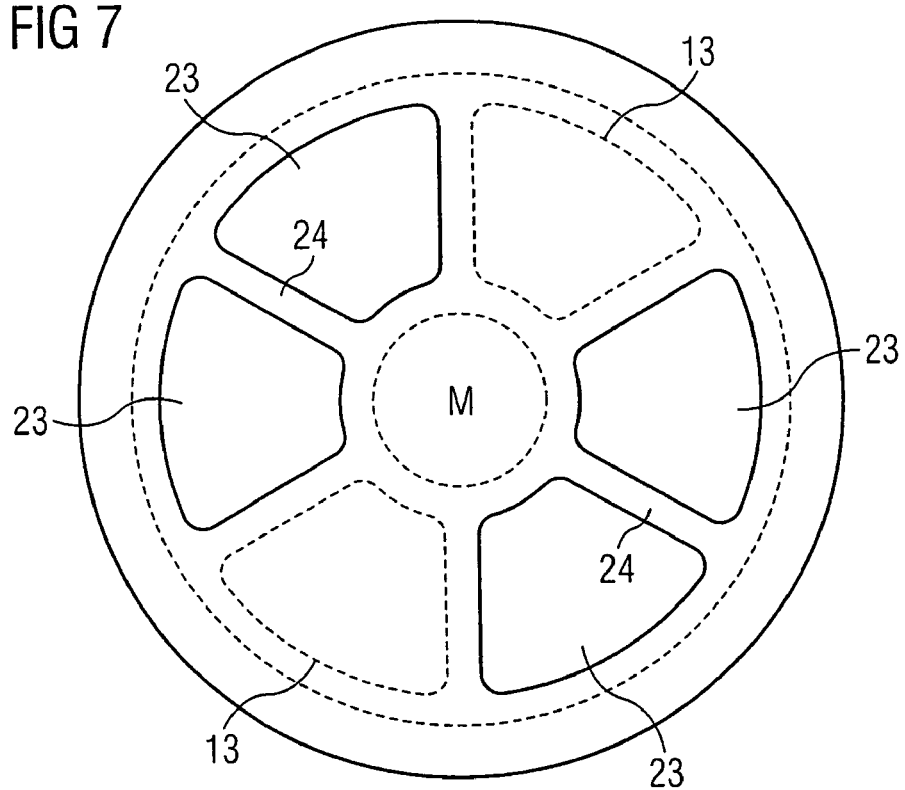

However, the number of bridges may be even larger. This is particularly advantageous where the blood flow passages are subdivided so as to be more symmetrically distributed over the cross section of the artificial valve 100, as has been discussed in relation to FIGS. 2 and 3. This is shown in FIG. 7 in conjunction with the artificial valve 100 shown in FIG. 5, but seen from the top similarly to FIG. 6. In this case, the blood flow passage 23 is divided to form two sections of about 120° equally spaced apart by relatively wide bridges, and such sections are further subdivided by bridges 24 so as to form subsections of equal size. Again, the bridges 24 are needed to prevent any backflow which would otherwise occur between adjacent valve members.

Figure 8:
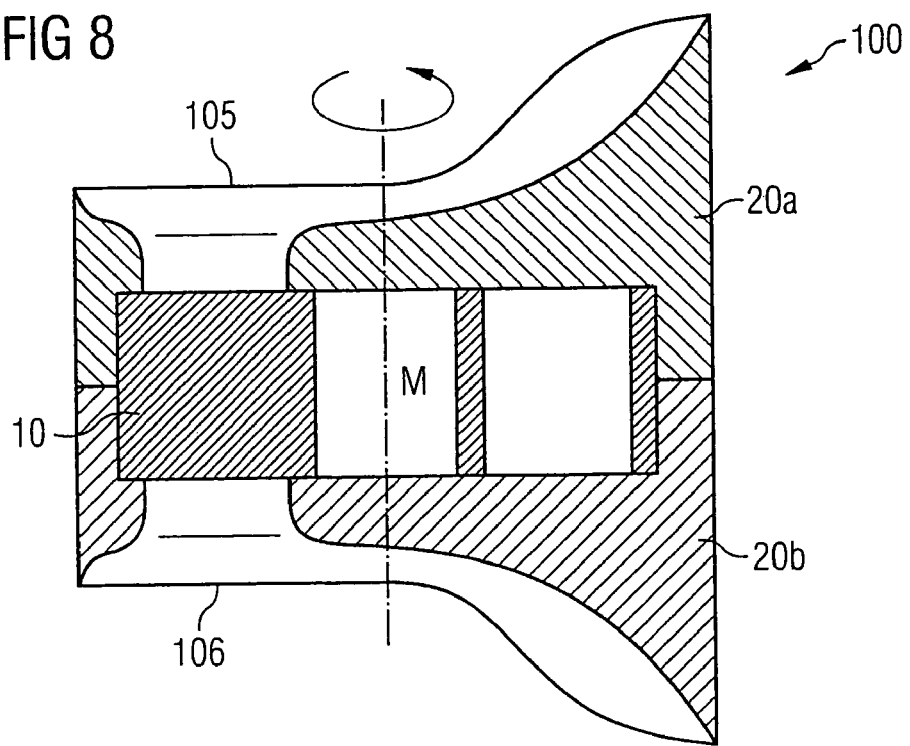
FIG. 8 shows an artificial valve with the upstream and downstream side being designed to provide for a laminar blood flow.

FIG. 8 shows an embodiment of an artificial valve with both the exterior surface 105 on the upstream side of the valve 100 and the exterior surface 106 on the downstream side thereof being designed to provide for a laminar blood flow along the entire surface area under in vivo conditions.

Figure 9:
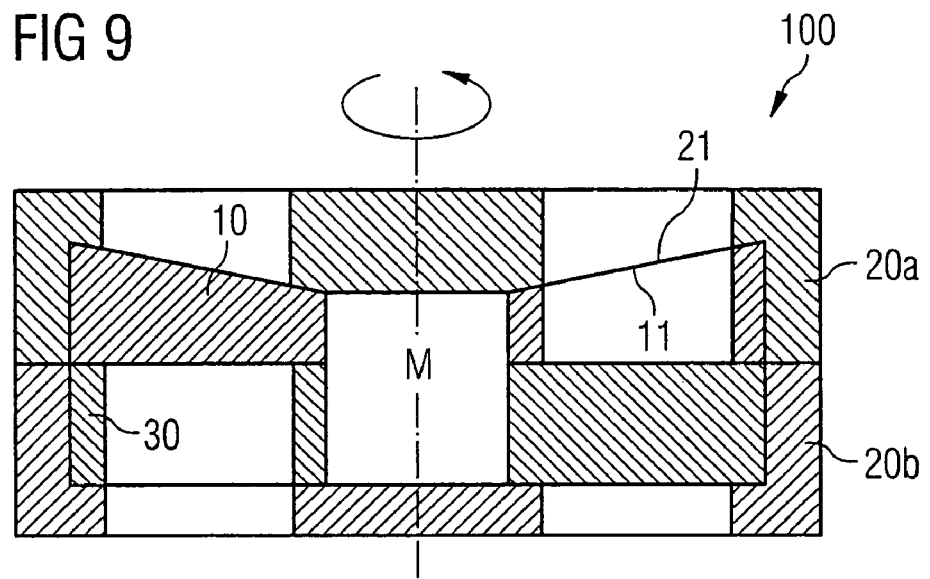
FIG. 9 shows an artificial valve with two contacting sealing surfaces having a concave and convex shape, respectively.

While in the afore described embodiments the displaceable valve members 10 and 30, respectively, are shown as being disc-shaped, this is not a requirement. FIG. 9 shows an embodiment in which the sealing surfaces 11, 21 of the first and second valve members 10, 20a have a concave and convex shape, respectively. The sealing surfaces between the first and third valve members 10, 30 and/or between the third and second valve members 30, 20b may also have a concave/convex shape either in the same or in an opposite direction.

Figure 10:
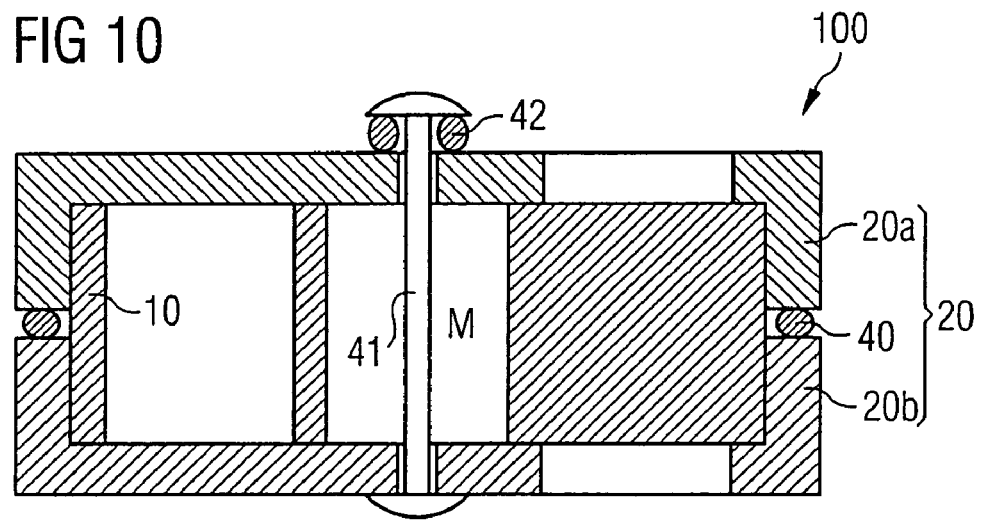
FIG. 10 shows an artificial valve in which the valve members are clamped by resilient means.

FIG. 10 shows an embodiment comprising pretensioning elements 40, 41, 42 by which the valve members 10, 20 are urged together. In this particular embodiment, the two halves 20a, 20b of the second valve member 20 forming the housing for accommodating therein the first valve member 10 are separated from each other by a first resilient sealing ring 40 made from a biocompatible polymer, such as polytetrafluoroethylene. A clamp 41 for clamping together the two halves 20a, 20b is provided and may have the form of a bolt, screw or the like extending through the two halves 20a, 20b, as shown in FIG. 10, or extending through only one of the two halves and fixed to the other of the two halves. A second resilient sealing ring 42 is provided not only to seal the interior of the artificial valve 100 against blood ingression but also to provide a constant pretensioning means in cooperation with the first sealing ring 40, which pretensioning should be small but sufficient to maintain contact between the sealing surfaces of the valve members.

Figure 11:
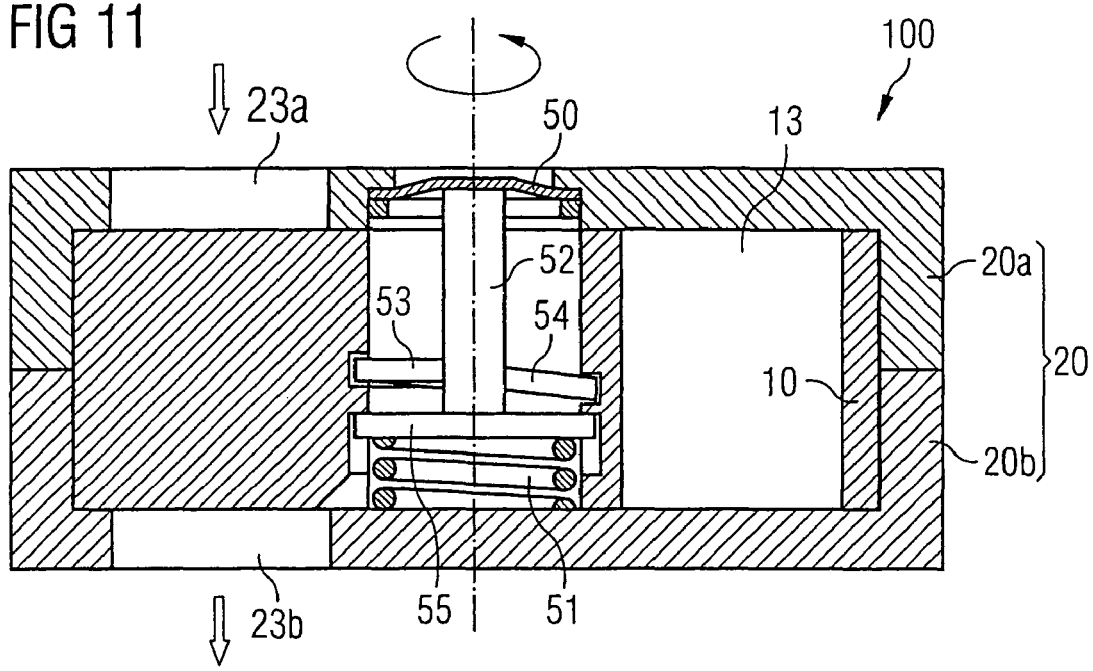
FIG. 11 shows a valve member with a mechanical displacing mechanism including a diaphragm and a return spring.

FIG. 11 shows a mechanical blood-pressure driven displacing mechanism driven by forces exerted by the blood pressure. The blood flow is indicated by two arrows. A diaphragm 50 is positioned on the upstream side of the valve 100. The diaphragm 50 may be made from a biocompatible polymer, preferably with a metal coating, or made only of metal, such as titanium or stainless steel. The diaphragm 50 is urged in an upstream direction by means of a return spring 51 via an intermediate piston 52. Upon blood pressure changes acting on the diaphragm 50, the piston 52 will move up and down. A pin 53 radially extending from the piston 52 is guided in a helical groove 54 of the displaceably arranged valve member 10 so that the piston 52 turns back and forth with each up and down movement of the piston 52. A bottom plate 55 of the piston 52 is connected to the displaceably arranged valve member 10 in such a manner that the valve member 10 turns along with the rotation of the piston 52, thereby aligning and disaligning the blood flow passage 13 of the first valve member 10 with the blood flow passages 23a, 23b of the halves 20a, 20b of the second valve member 20. Thus, the blood pressure is transformed into rotational movement of the first valve member 10. A return spring 51 urges the piston 52 against the force exerted by the blood pressure, thereby causing disalignment of the blood flow passages 10, 23a, 23b and, thus, closing of the valve 100 when the blood pressure on the upstream side of the valves decreases below a predetermined value.

Figure 12:
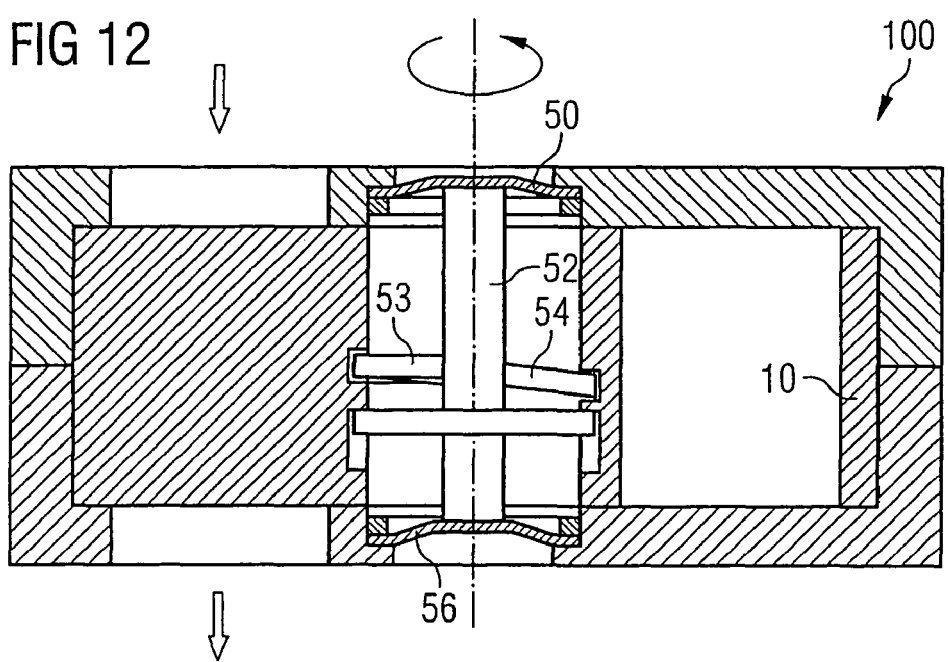
FIG. 12 shows an artificial valve with a mechanical displacing mechanism comprising a diaphragm on both the upstream and the downstream side of the valve.

FIG. 12 shows an artificial valve 100 with a slightly different mechanical blood-pressure driven displacing mechanism. Instead of the return spring 51, a second diaphragm 56 is provided on the downstream side of the valve so as to be actuated by the downstream blood pressure. Accordingly, when the artificial valve is e.g. used as a heart valve and the blood pressure in the heart chamber exceeds the blood pressure in the blood vessel downstream of the valve, the valve will open. In turn, when the heart relaxes and the heart chamber fills with blood again, the blood pressure on the downstream side of the valve will exceed the blood pressure in the heart chamber, thereby causing return movement of the first valve member 10 to the closed position shown in FIG. 12.

Instead of or in addition to a purely mechanical displacing mechanism, a motor M may be provided, as shown principally in FIG. 1. As shown in FIG. 13, a return spring 60 may be arranged for relative movement of the valve members 10, 20 so as to bring the flow passages 13, 23a, 23b into at least partial alignment. Thus, when the motor M blocks, the return spring 60 will override the motor.

There are various concepts of how a motor may be designed, arranged and driven in conjunction with the artificial valve of the present subject matter. FIG. 14 shows a preferred embodiment in which the motor M inside the artificial valve 100 is wirelessly driven by an electromagnetic field. The stator 70 for creating the electromagnetic field is positioned outside the blood vessel 200 in the form of an annular ring surrounding the blood vessel.

Wireless energy transfer to the motor from outside the blood vessel is preferable. While in the embodiment shown in FIG. 14 the wireless energy is directly consumed by the motor M, it is also possible to include in the valve an accumulator, such as a rechargeable battery and/or capacitor, that allows for transforming and accumulating wirelessly transferred energy so as to provide electric energy on demand.

Figure 15:
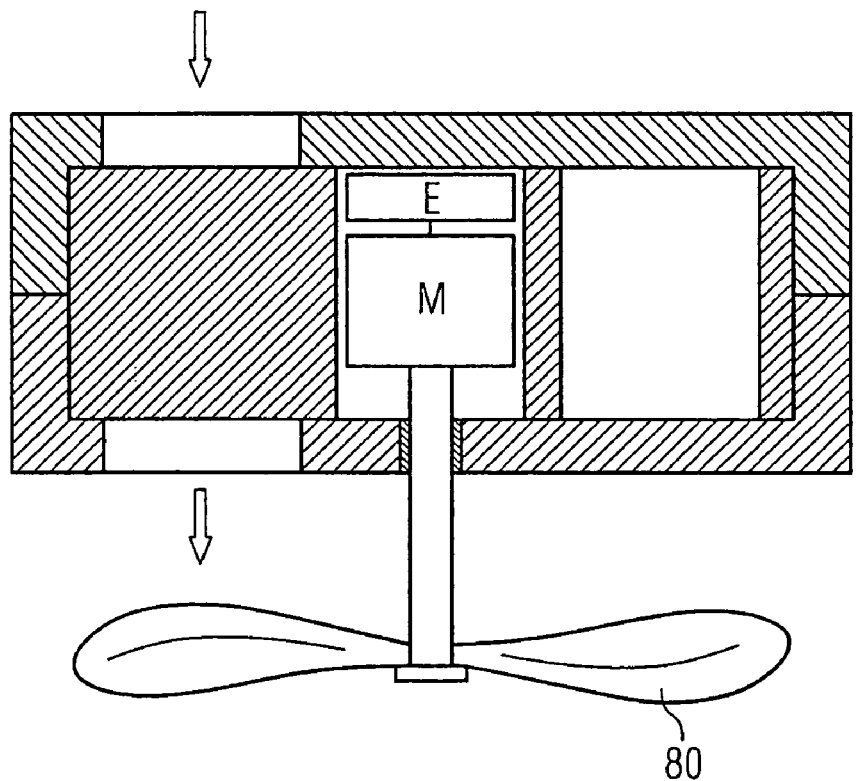
FIG. 15 shows an artificial valve where the energy for the motor is obtained from the blood flow by means of an impeller and comprising energy storage means for temporarily storing at least part of such energy.

FIG. 15 shows an embodiment in which the energy for the motor M is taken from the blood flow by means of an impeller 80. The amount of energy not directly consumed by the motor may be stored in an energy storage means E, such as a rechargeable battery and/or a capacitor and/or any other type of accumulator so as to be available upon demand. That way, an energy source outside the blood vessel can be dispensed with.

Figure 16:
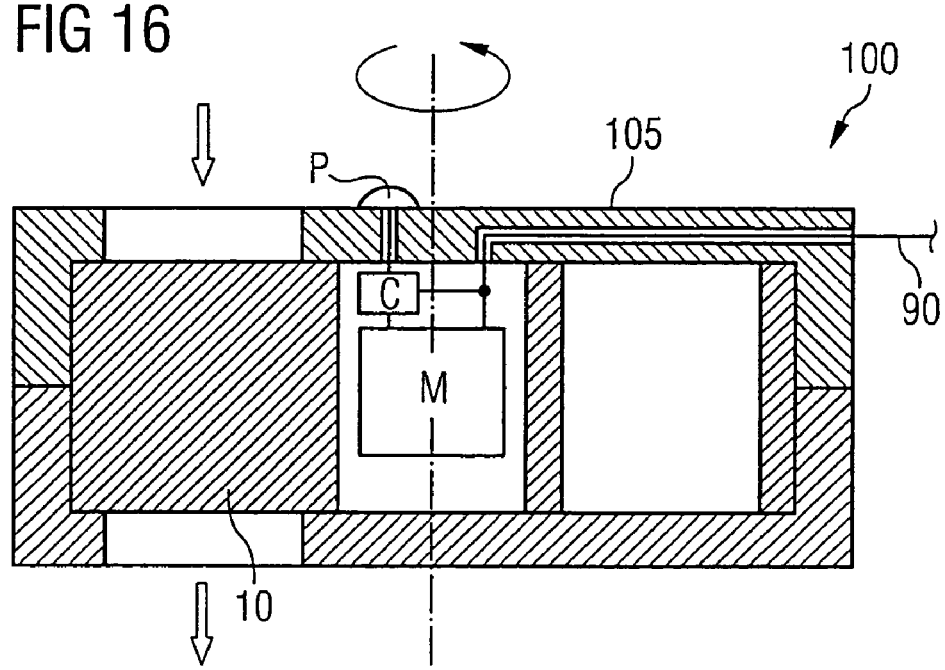
FIG. 16 shows various aspects of an artificial valve according to the present subject matter, including a pressure sensor on the upstream side of the valve, a galvanic connection from the motor to an external energy source and a control device incorporated in the valve for controlling the motor.

FIG. 16 shows an embodiment in which the motor M is supplied with energy via electric wires 90. Such wires may connect the motor M to a primary energy source and/or to energy storage means outside the blood vessel and even outside the patient's body. Although not shown in FIG. 16, energy storage means may also be provided within the artificial valve 100.

Furthermore, in the embodiment shown in FIG. 16 there is provided a control unit C. While the control unit C can alternatively be provided separate from the artificial valve 100 outside the blood vessel either in the patient's body or even outside the patient's body, it is preferred to have the control unit C proximate to the motor M. In FIG. 16, the control unit C is supplied with energy through the wires 90. The wires 90 may also serve to transfer data to the control unit C, e.g. during programming operations, to transfer feed back data in an opposite direction. Although not shown, transfer of energy and/or data to and from the control unit C may alternatively be performed wirelessly.

The control unit C controls the action of the motor M. In FIG. 16, a pressure sensor P is arranged on the exterior surface 105 on the upstream side of the valve 100. Pressure signals are continuously or intermittently sent to the control unit C so that the control unit C may cause the motor M to turn the displaceable valve member 10 as the pressure on the upstream side of the valve 100 exceeds an upper or a lower limit.

Alternatively or in addition the control signal of the control unit C may relate to a pacemaker signal. In that case, the pressure sensor P may perform the function of an alarm system indicating malfunction of the valve when the pressure on the upstream side of the valve exceeds a predetermined threshold. In such a case of malfunction, the control signal of the control unit will depend on the pressure sensor signal rather than on the pacemaker signal. Note that the pacemaker signal can alternatively serve directly as the control signal, in which case the pacemaker basically replaces the control unit C.

Figure 17:
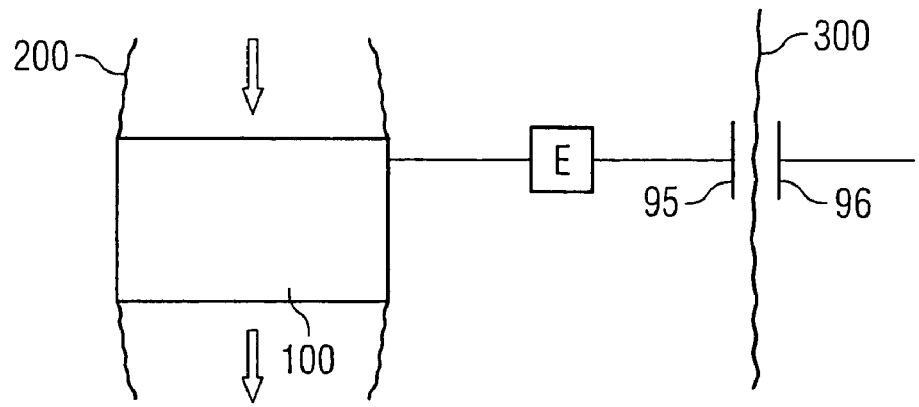
FIGS. 17 to 19 show examples of different embodiments of a valve system comprising the artificial valve according to the present subject matter.
Figure 18:
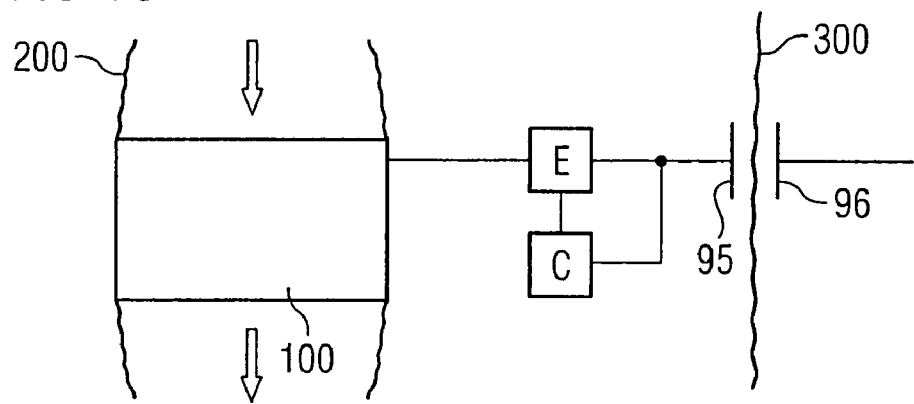
Figure 19:
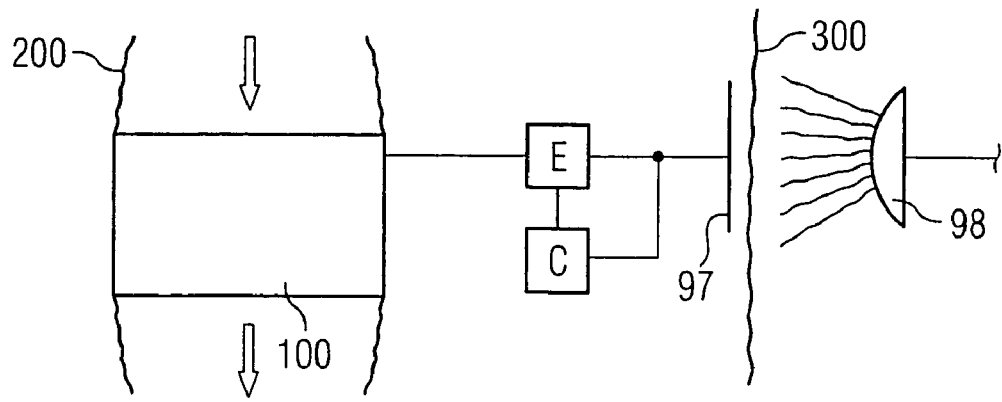

FIGS. 17 to 19 show three of a great number of possible arrangements of a valve system including an artificial valve 100 implanted in a blood vessel 200. It would unduly lengthen this specification if all ways of composing and combining the individual components of the valve system were described here in detail. It is therefore to be understood that the components so far described and the kind of energy and data transfer to, from and between these components—be it wireless or not—may be combined and arranged in any manner as long as it is not technically contradictive.

In FIG. 17, energy storage means E are arranged inside the patient's body outside the blood vessel 200. They are galvanically coupled to the artificial valve 100 and receive energy by wireless energy transfer through the patient's skin 300. A transmission interface 95 located under the patient's skin cooperates with a corresponding transmission interface 96 outside the patient's skin. Such interfaces 95, 96 may comprise antenna coils. Antenna coils are not only suitable for energy transfer but may simultaneously be used for transfer of data, such as by appropriate modulation of the energy signal or separately therefrom.

In a very basic embodiment of the subject matter, the energy storage means E shown in FIG. 17 may be dispensed with and the valve's valve members are actuated each time when energy is transferred via the transmission interfaces 95, 96.

In FIG. 18, the control unit C is implanted in the patient's body outside the blood vessel and controls the energy storage means E so as to activate energy transfer from the energy storage means E to the motor at appropriate times. The control unit C receives data and/or is programmable via the transmission interfaces 95, 96. Alternatively, although not shown in FIG. 18, one or both of the energy storage means E and the control unit C may form an integral part of the artificial valve 100 or may be located outside the patient's body, e.g. on the skin.

FIG. 19 shows an embodiment of the valve system similar to the one shown in FIG. 18 except for an alternative transmission interface being used. In this case, energy and/or data is transmitted by means of a wave signal, with such a wave signal penetrating through the patient's skin 300 onto a receiver 97. The receiver 97 is adapted to transform the radiation energy into electric energy and to demodulate any data information that is transmitted along with the radiation.

Implantation of the artificial valve 100 in a human being or an animal involves the steps of cutting the patient's skin, free-dissecting the blood vessel or heart 200, opening the blood vessel or heart, surgically affixing the artificial valve in place such that it forms a flow connection between an upstream part and a downstream part of the blood vessel or heart, and suturing the skin.

The valve may be fixed in place by means of suturing, such as by passing a suture thread through both the artificial valve and a wall of the blood vessel, e.g. through fixation holes in a wall of the artificial valve or through an adapter affixed to the artificial valve and composed of a biocompatible polymer, such as polytetrafluoroethylene or polyurethane.

Typically, the defective natural valve will be removed and, therefore, it will be necessary to dissect around the defective valve of the blood vessel either before or after putting into place the artificial valve.

As the valves of main interest are heart valves, in particular the aortic valve and sometimes the pulmonary valve, the patient's thorax will have to be opened to gain access to the heart. Subsequently, either a blood vessel adjoining the patient's heart, such as the aorta or pulmonary artery, will be opened to gain access to the patient's aortic valve and pulmonary valve, respectively, or an atrium of the patient's heart will be opened to gain access to either the right or left atrio-ventricular valve (tricuspid valve/bicuspid valve). Furthermore, it will in most cases become necessary to connect the patient to a heart-lung-machine.

In addition to the artificial valve, one or more additional components, as described above, may have to be implanted in the patient's blood vessel and/or within the patient's body outside the blood vessel to complete the overall valve system. Examples thereof are:

(a) the energy source for providing the motor 100 of the artificial valve with energy from outside the blood vessel,
(b) the energy storage means to provide the motor with energy, comprising at least one of a battery, a capacitor or a rechargeable battery,
(c) the galvanic coupling elements between either the energy source or the energy storage means and the motor for transmitting energy to the motor in contacting fashion, (d) the coupling elements adapted to connect either the motor or the energy storage means or both to an extra corporal primary energy source for transmitting energy to either the motor or the energy storage means or both in contacting fashion,
(e) the control unit C for controlling the motor so as to bring the blood flow passages of the artificial valve in and out of alignment in conformity with a control signal,
(f) the data transmission interface 95, 96; 97, 98 for wirelessly transmitting data from outside the patient's body to the control unit,
(g) a wireless programming interface for programming the internal control unit from outside the patient's body,
(h) the pacemaker, and
(i) the blood pressure sensor P.

As described previously, the artificial valve system, when installed on the patient's body, can be influenced from outside the patient's body. Such influence may relate to the control signal for controlling the valve's motor and may include:
(a) the step of providing the control signal from outside the patient's body,
(b) the step of transferring data between the extra corporal programming unit and the control unit of the artificial valve which provides the control signal to the motor, or
(c) the step of influencing the control signal by means of the pacemaker signal or directly providing the pacemaker signal as the control signal.

A method including the step of free-dissecting the patient's blood vessel may comprise the step of opening the patient's thorax or abdomen.

A method of treating a valve disorder in a blood vessel or heart of a patient may comprise the steps of inserting a needle-like tube into the thorax of a patient's body, filling the thorax with gas and thereby expanding the thorax cavity, placing at least two laparoscopic trocars in the patient's body, inserting a camera into the thorax, inserting a dissecting tool through the trocars and dissecting an area of the blood vessel or heart, opening the blood vessel or heart near a defective valve, positioning the artificial valve according to the subject matter to replace the function of the defective valve.

A method of treating a valve disorder in a blood vessel of a patient may also comprise the steps of inserting a needle-like tube into the abdomen of a patient's body, filling the abdomen with gas and thereby expanding the abdominal cavity, placing at least two laparoscopic trocars in the patient's body, inserting a camera into the abdomen, inserting a dissecting tool through the trocars and dissecting an area of the blood vessel, opening the blood vessel, and placing the artificial valve according to the subject matter in the blood vessel.

All methods as well as the features of the device may, if appropriate, be combined in any combination.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An artificial valve for implantation in a patient's blood vessel comprising:
    a first valve member of the artificial valve,
    a second valve member of the artificial valve,
    each of the first and second valve members having a first smooth surface on a first side of the respective valve member and a second surface on a second side of the respective valve member, opposite the first side of the respective valve member,
    the first smooth surface of the first valve member facing the first smooth surface of the second valve member so as to form a sealing contact between the first and second valve members,
    each of the first and second valve members further having at least one blood flow passage extending from the first surface of the respective valve member, completely through the respective valve member to the second surface of the respective valve member,
    at least one of the first and second valve members being arranged so as to be displaceable relative to the other valve member in a slidable manner, such that the blood flow passage of the second valve member can be brought into at least partial alignment with the blood flow passage of the first valve member while maintaining the sealing contact between the first and second valve members, and
    a displacing mechanism of the artificial valve for the displacement of the first and second valve members relative to one another, the displaceable arrangement of the first and second valve members relative to one another being such that the at least one displaceably arranged valve members is continuously slidable in one direction.

2. The artificial valve of claim 1, further comprising a third valve member having a first smooth surface arranged to form a sealing contact with the second surface of the first valve member and further having at least one blood flow passage extending from the first surface to a second surface located on an opposite side of the third valve member, wherein the third valve member is arranged so as to be displaceable relative to the first valve member in a slidable manner such that the passage of the third valve member can be brought into at least partial alignment with the passages of the first and second valve members while maintaining the sealing contact between the first and third valve members.

3. The artificial valve of claim 2, further comprising at least one further valve member having a first smooth surface for sealingly contacting a second surface of one of the other valve members and further having a blood flow passage for at least partial alignment with the passages of the other valve members.

4. The artificial valve of claim 1, wherein the valve members are rotatably slidable so as to allow for the at least partial alignment of their blood flow passages.

5. The artificial valve of claim 4, wherein the passages of the valve members are identically arranged about a common axis.

6. The artificial valve of claim 4, wherein the passages of the valve members have an interrupted or uninterrupted angular extension of exactly or preferably somewhat less than 360.times.n/(n+1) degrees, where n is the number of the displaceably arranged valve members.

7. The artificial valve of claim 4, wherein the passages of at least one of the valve members are divided into angularly extending sections by means of radially extending bridges.

8. The artificial valve of claim 7, wherein the number of bridges is n−1, where n is the number of the displaceably arranged valve members.

9. The artificial valve of claim 7, wherein the number of bridges is larger than n−1, where n is the number of the displaceably arranged valve members.

10. The artificial valve of claim 9, wherein the bridges of each valve member each have a center line, wherein the center lines are arranged about the common axis at an equal angular distance and the bridges each have an angular extension equal to or preferably somewhat larger than the angular extension of each of the sections of the angularly extending passages.

11. The artificial valve of claim 1, wherein at least two of the surfaces together forming a sealing contact are parallel.

12. The artificial valve of claim 11, wherein the sealing contact is overall flat.

13. The artificial valve of claim 1, wherein at least two of the surfaces together forming a sealing contact have a concave and convex shape, respectively.

14. The artificial valve of claim 1, wherein the valve members are made of a material inert enough to maintain over time a low friction between the surfaces forming the sealing contact.

15. The artificial valve of claim 14, wherein the material comprises a ceramic material.

16. The artificial valve of claim 1, wherein the sealing contact formed by two of the surfaces withstands without leaking an internal positive blood pressure of at least 80 mmHg (1.05 N/cm2).

17. The artificial valve of claim 16, wherein the two surfaces together forming said sealing contact each have a maximum roughness good enough to substantially avoid leakage through said sealing contact.

18. The artificial valve of claim 16, wherein the two surfaces together forming said sealing contact each have a maximum unevenness over the entire contact area good enough to substantially avoid leakage through said sealing contact.

19. The artificial valve of claim 16, wherein with respect of the two surfaces together forming said sealing contact, the minimum contact length between one of the corresponding passages and an outer border of one of the two surfaces is large enough to substantially avoid leakage through said sealing contact.

20. The artificial valve of claim 1, comprising at least one pretensioning element by which the valve members are urged together.

21. The artificial valve of claim 1, wherein an exposed surface of the valve on the upstream or downstream side or upstream and downstream side of the valve is designed to provide for a laminar blood flow along the entire surface area under in vivo conditions.

22. The artificial valve of claim 1, wherein the displacing mechanism is a blood-pressure driven mechanism, which is mechanically driven by forces exerted by the blood pressure.

23. The artificial valve of claim 22, wherein the blood-pressure driven displacing mechanism comprises a pressure transforming member arranged for transforming, when the valve is implanted in a patient's blood vessel, a blood pressure change into relative movement of the displaceably arranged valve members.

24. The artificial valve of claim 23, wherein the pressure transforming member comprises a pressure plate or diaphragm arranged to be moveable by changes of the blood pressure acting on the valve, and mechanically coupled to at least one of the displaceably arranged valve members.

25. The artificial valve of claim 24, wherein the pressure plate or diaphragm is positioned on an upstream side of the valve and coupled to the at least one of the valve members such that increased blood pressure acting on the valve on the upstream side of the valve causes the pressure plate or diaphragm to move in a downstream direction and thereby further causes at least partial alignment of the passages of the valve members.

26. The artificial valve of claim 24, wherein the pressure transforming member comprises a pressure plate or diaphragm positioned on a downstream side of the valve and coupled to the at least one of the valve members such that increased blood pressure acting on the valve on the downstream side of the valve causes disalignment of the passages of the valve members.

27. The artificial valve of claim 24, wherein the pressure plate or diaphragm is positioned on an upstream side of the valve and coupled to the at least one of the valve members such that increased blood pressure acting on the valve on the upstream side of the valve causes the pressure plate or diaphragm to move in a downstream direction and thereby further causes at least partial alignment of the passages of the valve members, and wherein the pressure transforming member comprises a pressure plate or diaphragm positioned on a downstream side of the valve and coupled to the at least one of the valve members such that increased blood pressure acting on the valve on the downstream side of the valve causes disalignment of the passages of the valve members, and wherein the pressure plate or diaphragm on the upstream side of the valve is rigidly connected to the pressure plate or diaphragm on the downstream side of the valve.

28. The artificial valve of claim 24, wherein resilient means are provided for urging the pressure plate or diaphragm positioned on the upstream side in an upstream direction.

29. The artificial valve of claim 1, wherein the displacing mechanism comprises a motor for bringing the blood flow passages of the valve members into and out of alignment.

30. The artificial valve of claim 29, wherein the motor is incorporated in the valve.

31. The artificial valve of claim 30, wherein the motor is contained within a valve housing formed and sealed against blood ingression by the valve members.

32. The artificial valve of claim 29, wherein the motor is arranged for being driven by an electromagnetic field.

33. The artificial valve of claim 29, wherein means are provided to urge the blood flow passages into at least partial alignment when the motor is not energized.

34. The artificial valve of claim 29, wherein the displacing mechanism is provided with an energy source for the motor, said energy source to be implanted in a blood vessel along with the valve.

35. The artificial valve of claim 34, wherein the energy source for the motor comprises a blood flow energy transforming device for transforming blood flow energy into electrical energy, when the energy source is implanted in a patient's blood vessel.

36. The artificial valve of claim 35, wherein the blood flow energy transforming device comprises an impeller.

37. The artificial valve of claim 35, wherein the displacing mechanism further comprises an energy storage device for temporarily storing the transformed electrical energy.

38. The artificial valve of claim 37, wherein the energy source includes a capacitor.

39. The artificial valve of claim 34, wherein the energy source comprises a rechargeable battery.

40. The artificial valve according to claim 29 further comprising a control unit for controlling the motor of the valve so as to bring the blood flow passages into and out of alignment in conformity with a control signal.

41. The artificial valve of claim 40, wherein the control unit is adapted for controlling the motor from outside the patient's body.

42. The artificial valve of claim 40, wherein the control unit is adapted for implantation inside the patient's body outside the blood vessel.

43. The artificial valve of claim 40, wherein the control unit is adapted for implantation inside the blood vessel.

44. The artificial valve of claim 43, wherein the control unit is integrated in the artificial valve.

45. The artificial valve of claim 40, further comprising a control signal transmission device for wireless transmission of the control signal.

46. The artificial valve of claim 45, comprising a data transmission interface for wirelessly transmitting data from outside the patient's body to the control unit inside the patient.

47. The artificial valve of claim 45, wherein the wireless control signal and/or data transmission comprises an electromagnetic wave signal, including at least one of an infrared light signal, a visible light signal, an ultra violet light signal, a laser signal, a microwave signal, a radio wave signal, an X-ray radiation signal, and a gamma radiation signal.

48. The artificial valve of claim 45, wherein the wireless control signal comprises a sound or ultrasound wave signal.

49. The artificial valve of claim 45, wherein the wireless control signal comprises a digital or analog signal or a combination thereof.

50. The artificial valve of claim 40, adapted to transmit the control signal in the same manner as energy is transmitted to the motor.

51. The artificial valve of claim 50, adapted for transmitting the control signal by modulation of an energy signal.

52. The artificial valve of claim 40, adapted to provide the control signal as at least one of a frequency, phase and amplitude modulated signal.

53. The artificial valve of any of claims 50 to 52, wherein the control signal is influenced by external signals.

54. The artificial valve of claim 53, wherein the control signal relates to a blood pressure signal.

55. The artificial valve of claim 54, further comprising a blood pressure sensor, said blood pressure sensor providing the blood pressure signal, when the system is installed on a patient.

56. The artificial valve of claim 55, wherein the blood pressure sensor is arranged on an upstream side of the valve.

57. The artificial valve of claim 55, wherein the blood pressure sensor is fixed to the valve.

58. The artificial valve of claim 56, wherein the blood pressure sensor is provided for being located in a heart chamber.

59. The artificial valve of claim 53, wherein the control signal relates to a pacemaker signal.

60. The artificial valve of claim 40, further comprising a pacemaker, said pacemaker, when the system is installed on a patient, directly providing the control signal or influencing the control signal.

61. The artificial valve of claim 40, wherein the control unit is freely programmable so as to be flexibly adaptable to provide control signals for the motor according to changing demands.

62. The artificial valve of claim 61, wherein the control unit is programmable from outside the patient's body.

63. The artificial valve of claim 61, comprising a programming unit adapted for programming the control unit.

64. The artificial valve of claim 62, wherein the control unit is adapted for implantation inside the patient's body and is programmable by wireless remote control.

65. The artificial valve of claim 40, wherein the control unit is adapted to provide feedback information.

66. The artificial valve of claim 65, wherein the feedback information relates to physiological data of the person, such as blood pressure data.

67. The artificial valve of claim 65, wherein the feedback information relates to technical data of the valve system.

68. A valve system comprising an artificial valve for implantation in a patient's blood vessel comprising:

a first valve member of the artificial valve,
a second valve member of the artificial valve,
each of the first and second valve members having a first smooth surface on a first side of the respective valve member and a second surface on a second side of the respective valve member, opposite the first side of the respective valve member,
the first smooth surfaces of the first and a second valve members facing each other so as to form a sealing contact between the first and second valve members,
the first and second valve members further having at least one blood flow passage extending completely through the respective valve member from the first surface of the respective valve member to the second surface of the respective valve member,
at least one of the valve members being arranged so as to be displaceable relative to the other valve member in a slidable manner such that the blood flow passage of the second valve member can be brought into at least partial alignment with the blood flow passage of the first valve member while maintaining the sealing contact between the first and second valve members, and
a displacing mechanism of the artificial valve for the relative displacement of the first and second valve members, the displacing mechanism comprising a motor for displacing the at least one displaceably arranged valve member continuously in one direction and thereby bringing the blood flow passages of the first and second valve members into and out of alignment, and
an energy source for providing the motor with energy from outside the blood vessel.

69. The valve system of claim 68, wherein the energy source is adapted to provide energy from outside the patient's body to the motor for use by the motor at the time the energy is transferred.

70. The valve system of claim 69, further comprising an energy transmission device for wireless energy transfer from the energy source outside the patient's body to the motor.

71. The valve system of claim 68, wherein the energy source comprises energy storage means.

72. The valve system of claim 71, further comprising an energy transmission device for wireless energy transfer from the energy storagemeans to the motor.

73. The valve system of claim 72, further comprising an energy transmission device for wireless energy transfer from outside the patient's body to the energy storage means, said energy storage means being adapted to be implanted inside the patient's body.

74. The valve system of claim 70 or 72, wherein the energy transmission device for wireless energy transfer is adapted to generate an electromagnetic field.

75. The valve system of claim 70 or 72, wherein the energy transmission device for wireless energy transfer is adapted to generate a magnetic field.

76. The valve system of claim 70 or 72, wherein the energy transmission device for wireless energy transfer is adapted to generate an electrical field.

77. The valve system of claim 70 or 72, wherein the energy transmission device for wireless energy transfer transmits energy by at least one wireless signal.

78. The valve system of claim 77, wherein the wireless energy signal comprises an electromagnetic wave signal, including at least one of an infrared light signal, a visible light signal, an ultra violet light signal, a laser signal, a micro wave signal, a microwave signal, an X-ray radiation signal, and a gamma radiation signal.

79. The valve system of claim 77, wherein the wireless energy signal comprises a sound or ultrasound wave signal.

80. The valve system of claim 77, wherein the wireless energy signal comprises a digital or analog signal or a combination thereof.

81. The valve system of claim 71, wherein the energy storage means comprises at least one of a battery, a capacitor, a rechargeable battery and any other type of accumulator.

82. The valve system of claim 71, wherein the energy storage means is adapted to be implanted inside the patient's body.

83. The valve system of claim 82, wherein the energy storage means is adapted to be implanted inside the blood vessel.

84. The valve system of claim 82, wherein the energy storage means is adapted to be implanted outside the blood vessel.

85. The valve system of claim 82, further comprising galvanic coupling elements adapted to connect the energy storage means, when implanted inside the patient's body, to an extra corporal primary energy source for transmitting energy to the energy storage means in contacting fashion.

86. The valve system of claim 85, further comprising the extra corporal primary energy source.

87. The valve system of claim 68, wherein the motor is adapted to directly transform the wirelessly transferred energy into kinetic energy.

88. The valve system of claim 68, comprising a transforming device for transforming wirelessly transferred energy into electric energy.

89. The valve system of claim 68, further comprising galvanic coupling elements for coupling with the motor for transmitting energy to the motor in contacting fashion.

90. The valve system of claim 54, further comprising an alarm system.

91. The valve system according to claim 90, wherein the alarm system comprises a blood pressure sensor.

92. The valve system of claim 91, wherein the blood pressure sensor is arranged on an upstream side of the valve.

93. The valve system of claim 91, wherein the blood pressure sensor is fixed to the valve.

94. The valve system of claim 92, wherein the blood pressure sensor is provided for being located in a heart chamber, when the system is installed on a patient.

* * * * *